United States Patent [19]
Carr et al.

[11] Patent Number: 5,690,614
[45] Date of Patent: Nov. 25, 1997

[54] MICROWAVE APPARATUS FOR WARMING LOW FLOW RATE INFUSATES

[75] Inventors: Kenneth L. Carr, Harvard; James Regan, Waltham, both of Mass.

[73] Assignee: Microwave Medical Systems, Inc., Acton, Mass.

[21] Appl. No.: 524,392

[22] Filed: Sep. 6, 1995

[51] Int. Cl.$^6$ .................................................. A61F 7/12
[52] U.S. Cl. .................................. 604/114; 219/687
[58] Field of Search ............ 604/113–114; 219/687–689

[56] References Cited

U.S. PATENT DOCUMENTS 3,963,892  6/1976  Camph et al. .
4,614,514  9/1986  Carr et al. .
4,715,727  12/1987  Carr .
5,073,167  12/1991  Carr et al. .

OTHER PUBLICATIONS

Biodmedical Thermology, pp. 257–268, 1982 Alan R. Liss, Inc. NY, Heating Blood in extracorporal Circulation with a High–Frequency Electromagnetic Field: Effect of Microwaves on Blood J. Andre, et al.

*Primary Examiner*—Mark Bockelman
*Attorney, Agent, or Firm*—Cesari and McKenna, LLP

[57] ABSTRACT

Microwave heating apparatus for warming low flow rate infusates includes an electrically conductive housing defining an elongated heating cavity and a printed circuit board which separates the cavity lengthwise into first and second cavity sections. The circuit board includes a substrate which provides a fluid-tight divider between the two cavity sections and a meandering conductor run which extends along the substrate.

17 Claims, 2 Drawing Sheets

5,690,614

MICROWAVE APPARATUS FOR WARMING LOW FLOW RATE INFUSATES

FIELD OF THE INVENTION

This invention relates in general to microwave warming apparatus for blood and intravenously fed fluids. It relates especially to such apparatus which can handle low fluid rates and also provides close control over the temperature of the fluid being warmed.

BACKGROUND OF THE INVENTION

In the medical field, there exists a number of applications requiring the warming of blood and IV fluids. For example, in connection with cardiac surgery during extracorporeal circulation, the patient is first cooled in order to slow metabolism and thereafter there is a requirement that the circulating blood be warmed. Another application is the warming of blood or intravenous fluids is in a trauma situation. For example, heated IV fluids are useful in hypothermic patients and in trauma patients requiring massive IV resuscitation.

One common technique for warming blood is to pass the blood through coils immersed in a warm water bath. Microwave heating has also been employed in connection with the warming of blood and IV fluids. An example of an in-line microwave warmer for blood and IV fluids is described in U.S. Pat. No. 5,073,167. That apparatus is advantageous because it monitors the liquid temperature radiometrically and controls the heating power level based on the temperature measurements taken so that close control is maintained over the temperature of the fluid being warmed. Typically, the fluid exiting the warmer should have a temperature close to normal body temperature, i.e., 37° C.

However, the fluid exiting the conventional blood warmers immediately begins to cool to room temperature and this cooling increases as the rate of infusion slows and the length of the patient IV line increases. In many cases, the warm IV fluid may sit in the patient line, slowly dripping its way to the patient's IV site. The constant exposure of the fluid to room temperature, e.g., 20° C., steadily reduces the temperature of the fluid. In many cases, the volume of fluid infused at a low flow rate may be quite large relative to the size of the patient, particularly, in pediatric and neonate applications, causing a significant decrease in the patient's temperature.

In actuality, in the year 1989, blood transfusions of 1 to 2 units at flow rates less than 25 ml./min. accounted for more than 60% of the 3.2 million U.S. patients who received a total of 12.1 million units of red blood cells. Fluid exiting a typical warmer with a temperature of 37° C. at a flow rate of 100 ml./hour cooled to 24.4° C. after traveling through a typical length (105 cm) of patient IV tubing; see Farlos G, Johnston C, Pruitt KM, Plouff RT: "Temperature Relationship To Distance And Flow Rate Of Warmed IV Fluid", ANN EMERG MED 20: 1189–1200, 1991.

Recently, a warmer has been developed to address low flow rate warming. The design uses a water jacket to surround the patient IV line. The water jacket, in turn, connects to a pole-mounted water bath maintained at a temperature of about 40° C. by a 300 watt heater and circulating pump. Thus, the device surrounds the patient line with a layer of circulating warm water all the way to the patient and thus substantially eliminates patient line cool down. However, that device is disadvantaged because the water jacketed tubing is relatively large in diameter and inflexible making it difficult to attach to the catheter which introduces the infusate into the patient and adding mechanical stress at the catheter connection. Because of this, it has been found necessary to add a short length of non-insulating IV tubing between the jacketed tubing and the catheter.

Also, there is always a risk associated with the use of warm water for heating because of the danger of infection. Bacteria grows rapidly in warm water, requiring great care to prevent contact between the warm water and the tubing interconnections during a warming procedure. Also, to ensure sterility, the warm water bath must be emptied and cleaned regularly to avoid possible contamination.

SUMMARY OF THE INVENTION

Accordingly, it is an object of the present invention to provide apparatus for warming blood and IV fluids rapidly and uniformly independent of changes in the fluid inlet temperature and flow rate.

Another object of the invention is to provide such apparatus which is quite small and compact so as to allow fluid warming in close proximity to the patient, dramatically reducing the length of the patient line between the warmer and the patient.

Still another object of the invention is to provide warming apparatus which uses microwave energy to warm the blood or other fluid.

A further object of the invention is to provide apparatus of this type which accurately controls the temperature of the fluid being warmed through the use of passive, non-invasive radiometric sensing.

A further object of the invention is to provide apparatus for warming blood and IV fluids which is portable for field or ambulance use.

Yet another object of the invention is to provide such apparatus whose portion contacted by the fluid being warmed is fully disposable and relatively inexpensive to make.

Other objects will, in part, be obvious and will, in part, appear hereinafter.

The invention accordingly comprises the features of construction, combination of elements and arrangement of parts which will be exemplified in the following detailed description, and the scope of the invention will be indicated in the claims.

Briefly, the apparatus comprises a small, disposable in-line fluid warmer which may be connected to the patient IV line in close proximity to the insertion site at the patient. Basically, the warmer is a microwave integrated circuit comprising a microwave heating cavity which is divided lengthwise by a printed circuit board which carries a printed center conductor configured as a meander line. The infusate being warmed, which has a relatively high dielectric constant, flows through the cavity volume at one side of the circuit board and forms the base material of the microwave integrated circuit. The volume of the cavity at the other side of the circuit board is filled with air which has a low dielectric constant so that substantially all of the lines of microwave energy will be confined to the infusate-filled portion of the cavity.

The warming apparatus also includes a solid state programmable transmitter for delivering microwave energy to the cavity and a sensor for sensing the temperature of the infusate leaving the cavity. When the sensor is a non-invasive sensor such as a radiometer, a diplexer may be used to separate the microwave heating frequency from the received or radiometer frequency thus allowing the use of a common coaxial cable connection to the heating cavity.

When the apparatus is in operation, the microwave integrated circuit comprised of the cavity and the infusate therein is of sufficient length to attenuate the microwave energy from the transmitter and to provide a good match at the operating frequency of the transmitter.

The present warming apparatus is able to deliver infusate at precisely controlled temperature e.g., 37° C., at fluid flow rates of 1 to 25 ml./min. Since the heating cavity section of the apparatus is quite small and can be located quite close to the patient, the temperature of the fluid infused into the patient is substantially the same as the temperature of the fluid leaving the heating cavity. Thus, the apparatus can deliver fluids at normothermic temperatures even at low fluid flow rates. Therefore, the apparatus should prove to be quite useful for the prevention of hypothermia, particularly in small patients.

Yet, because the heating cavity portion of the apparatus, which is the disposable part, comprises only a few simple components which are relatively inexpensive to manufacture in quantity, the overall apparatus is quite affordable. Therefore, the warmer should find wide application particularly in situations requiring the warming of blood and other IV fluids infused at low flow rates.

BRIEF DESCRIPTION OF THE DRAWINGS

For a fuller understanding of the nature and objects of the invention, reference should be had to the following detailed description taken in connection with the accompanying drawings, in which.

DESCRIPTION OF THE PREFERRED EMBODIMENT

Figure 1:
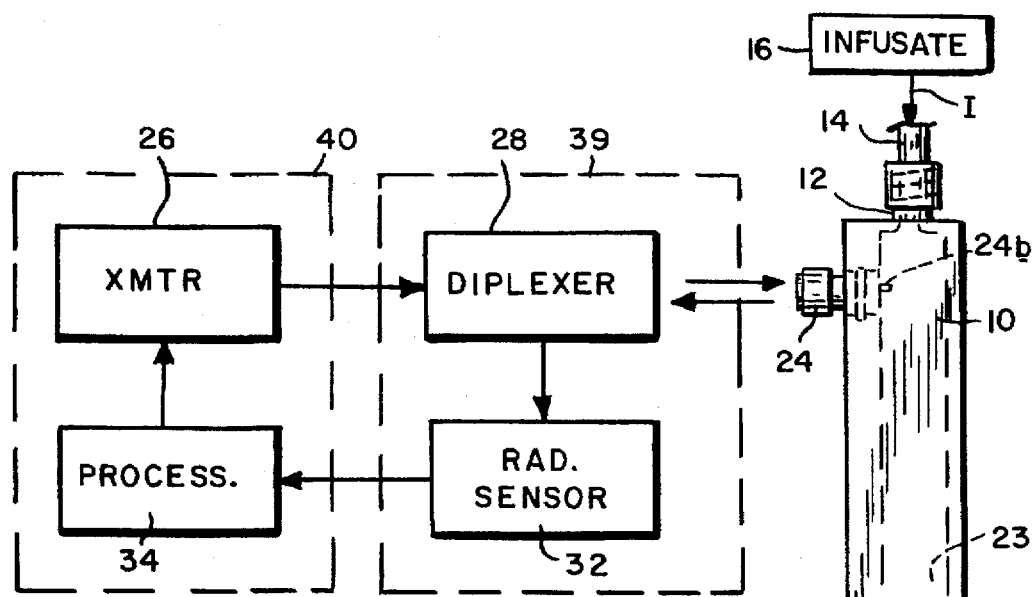
FIG. 1 is a diagrammatic view of microwave infusate warming apparatus embodying the invention.

Referring to FIG. 1 of the drawing, the warming apparatus includes an in-line, flow-through fluid warmer 10 having fluid inlet fitting 12 adapted to be connected by an IV line 14 to an infusate source 16, e.g., a blood bag. The warmer 10 also has an outlet fitting 18 for connection by an IV line 20 to an infusate destination such as a transcutaneous catheter in a patient. Fittings 12 and 18 may be standard Leur-lock connectors, for example.

The warmer 10 is actually a microwave integrated circuit comprising a microwave heating cavity 23 inside warmer 10 and the infusate I flowing from inlet 12 through cavity 23 to the outlet 18. The cavity 23 receives microwave energy via a coaxial connector 24 (e.g. 50 ohms) from a microwave transmitter 26 whose output is coupled to connector 24 by way of a diplexer 28. The microwave energy conducted to the heating cavity 23 is attenuated by the infusate I flowing through the cavity, which fluid is highly absorbent at the microwave frequency of transmitter 26, e.g., 2450 Mhz to minimize cable loss, 915 MHz. In the process, the infusate absorbs energy and becomes heated so that it leaves warmer 10 at an elevated temperature.

The apparatus also includes a radiometric sensor or radiometer 32 which is connected by way of the diplexer 28 to the heating cavity connector 24. Sensor 32 monitors the temperature of the infusate in the heating cavity. Preferably, the sensor is responsive at a signal frequency much higher than the transmitter frequency, e.g., 4.0 GHz. The output of the sensor 32 is applied to a processor 34 which controls the power output of the microwave transmitter 26 to maintain the temperature of the infusate leaving cavity 23 at a selected substantially constant value, e.g., 34° C.

Preferably, the diplexer 28 and sensor 32 form a single unit 39 which is located close to the warmer and is connected thereto by a coaxial cable. The transmitter 26 and processor 34, on the other hand, may form another unit 40 located relatively remote from the warmer and connected to unit 39 by a suitable cable.

Refer now to FIGS. 2 to 5 which show the components of warmer 10 in greater detail. The warmer includes an electrically conductive housing 40, e.g. of aluminum metal or metallized plastic, consisting of an upper, shell-like section 42 and a similar lower shell-like section 44 and which functions as a guided wave structure at the operating frequency of transmitter 26. The overall dimensions of the warmer are quite small, e.g., 4½×1×⅝ in.

Housing section 42 is formed with a generally rectangular cavity section 46 which extends almost the entire length of section 42. Also, a semi-cylindrical groove or side channel 48 extends in from one side of section 42 near one end thereof so that it intercepts cavity section 46.

The lower section 44 is likewise formed with a similar length cavity section 52 and a semi-cylindrical side channel or groove 54. Also present in the lower section 44 are a pair of end openings 56 which lead to the fluid inlet fitting 12 and outlet fitting 18 of warmer 10. Actually, to minimize cost, these fittings may be molded integrally with housing section 44. The cavity sections 46, 52 and the channels, 48, 54 in housing sections 42 and 44, respectively, are arranged so that they are disposed opposite one another. Thus, the two sections 42 and 44 are essentially mirror-images of one another except for the presence of the end openings 56 in section 44.

Figure 2:
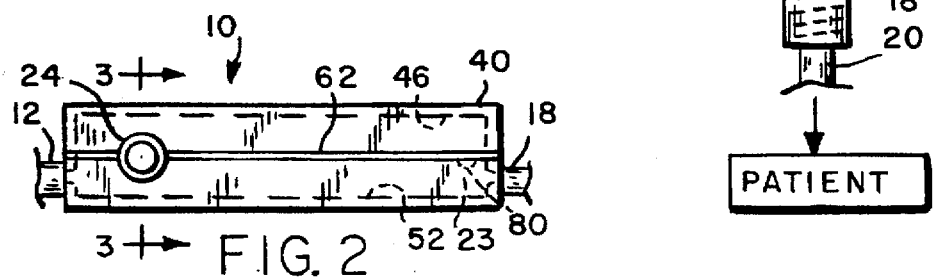
FIG. 2 is a view in side elevation of the disposable warming portion of the FIG. 1 apparatus.
Figure 3:
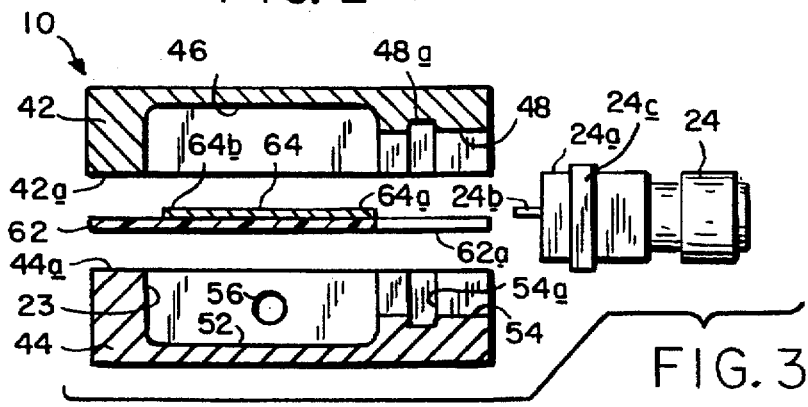
FIG. 3 is an exploded sectional view, on a larger scale, taken along line 3—3 of FIG. 2.
Figure 4:
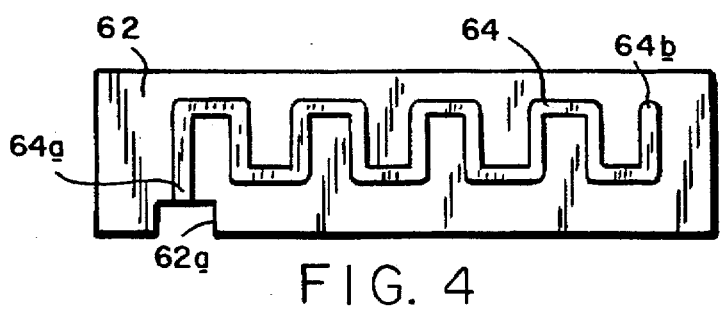
FIG. 4 is a plan view of a dividing circuit board present in the warming portion depicted in FIGS. 2 and 3.

Warmer 10 also includes a generally rectangular printed circuit board 62. The printed circuit board has the same length and width dimensions as sections 42 and 44 and it is sandwiched between those sections such that the opposing surfaces 42a and 44a of those sections engage opposite faces of the printed circuit board as shown in FIG. 2. The circuit board 62 substrate should be of a fluid-impervious material, e.g., PTFE-impregnated fiberglass and be of such thickness e.g., 5 mils., that the circuit board 62 provides a fluid-tight divider between the cavity sections 46 and 52 in the two housing sections.

Circuit board 62 carries a printed conductor run 64, e.g., of copper, 5 configured as a meander line, which extends along the printed circuit board. One end 64a of the conductor run extends to a slot 62a in the side of the printed circuit board 62 which, when the circuit board is sandwiched between the two housing sections, is located directly between the channels 48 and 54 formed in the two housing sections. Prior to securing the housing sections 42 and 44 together on opposite sides of the printed circuit board 62, the inner end 24a of connector 24 is positioned in slot 62a of circuit board 62. When positioned thusly, the center conductor 24b of the connector contacts the adjacent end 64a of the printed conductor and those two elements may be electrically connected together by solder S (FIG. 5), or the like.

Preferably, the inner end segment of connector 24 has a raised rib 24c which may engage in grooves 48a and 54a formed in channels 48 and 54, respectively, when the two housing sections 42 and 44 are brought together on opposite sides of circuit board 62. The sections may then be permanently secured together by suitable means such as an adhesive, welds, fasteners or the like. When so secured, they clamp connector 24 between them making good electrical connection to the outer conductor of that connector.

Alternatively, connector 24 may be molded into housing 40 at the time the housing is formed.

In the illustrated warmer 10, the cavity section 52 in housing section 44, which is sealed off by the circuit board 62, conveys the infusate I from inlet fitting 12 to outlet fitting 18. The infusate flowing through cavity section 52 and which has a relatively high dielectric constant, functions as the base material of a microwave integrated circuit formed by the cavity, the housing 40 constituting the ground plane for the cavity. On the other hand, the cavity section 46 at the opposite side of circuit board 62 is filled with air or other material having a relatively low dielectric constant. Therefore, when microwave energy is coupled to the conductor 64 of circuit board 62 by way of connector 24, a high delta constant exists so that substantially all the lines of energy are concentrated in the cavity section 52 containing the infusate. Also, housing section 42 provides a shield against radiation produced by warmer 10.

Preferably, but not necessarily, the printed conductor 64 is on the side of circuit board 62 facing away from the cavity section 52 so that it is not affected by the infusate I. The infusate flowing through the cavity section 52, being lossy, is highly absorbent at the microwave frequency of transmitter 26 and hence attenuates the microwave energy in the heating cavity 23. Preferably, the running length of the meandering conductor 64 should be long enough to attenuate all of the microwave energy and provide a good impedance match, and thus low reflection, within the cavity. We have found, for example, that a warmer 10 with a sinuous conductor 64 about 3⅜ in. long and having ¼ in. long legs operates satisfactorily. The output end 64b of printed conductor 64 can either provide an open circuit as shown or shorted to housing 40.

Figure 5:
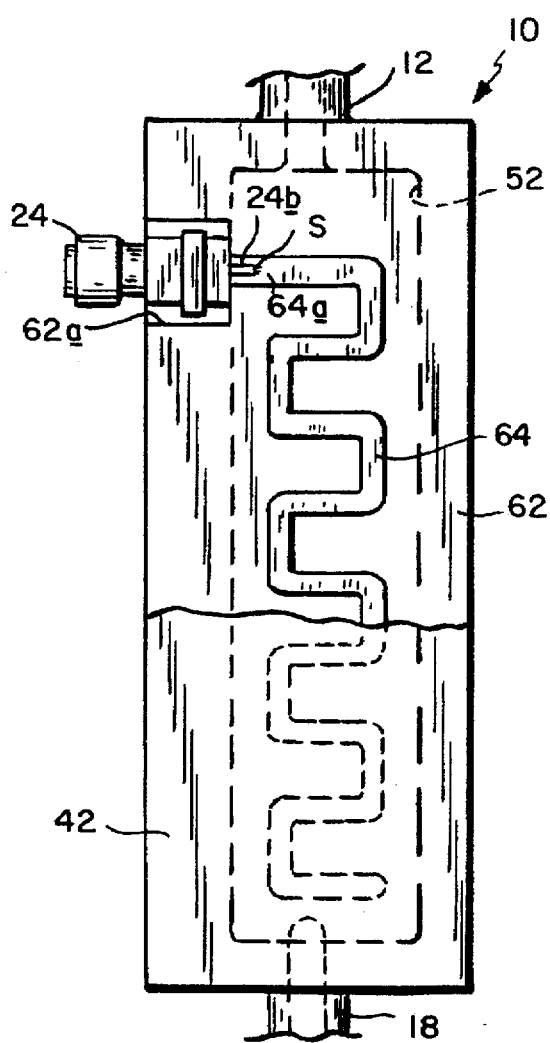
FIG. 5 is a plan view with parts broken away of that warming portion.
Figure 5A:
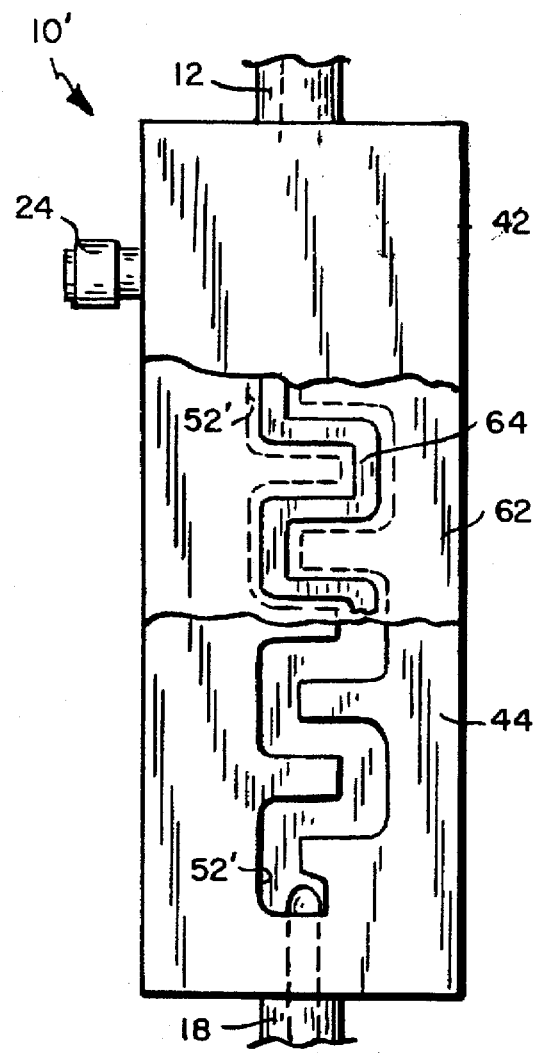
FIG. 5A is a similar view of a second warming portion embodiment.

It should be understood that it is not necessary that the cavity section 52 in the lower housing section 44 extend the full width of the housing, only that it be present opposite the meandering conductor 64. For example, FIG. 5A illustrates a warmer 10' which is substantially the same as warmer 10 except that the lower housing section has a cavity section 52' in the form of a meandering channel which extends between inlet and outlet opening 56 and which follows the course of the meandering conductor 64 in that warmer. Thus, all of the infusate flowing through the warmer 10' is exposed to the electromagnetic energy developed in cavity section 52' to substantially the same degree, resulting in uniform heating and maximum heating efficiency.

In the FIG. 5A warmer 10' the upper cavity section may also be a meandering channel, i.e., a mirror image of section 52'.

Referring to FIG. 1, transmitter 26 is preferably a solid state programmable transmitter which may operate at 915 Mhz and have a maximum power output of 25 watts. Such a transmitter is available from Microwave Medical Systems, Inc. Action, Mass. That transmitter provides, if desired, short term operation with battery backup and automatic battery recharging when the unit is plugged into an operative AC outlet. Also, detector circuits are provided in the transmitter to measure both forward and reflected power.

The radiometer 32 is also available from Microwave Medical Systems, Inc. That unit has a physical volume of about 2 cubic inches and weighs only about 3 oz. It has a center frequency of 4.0 GHz.

Figure 6:
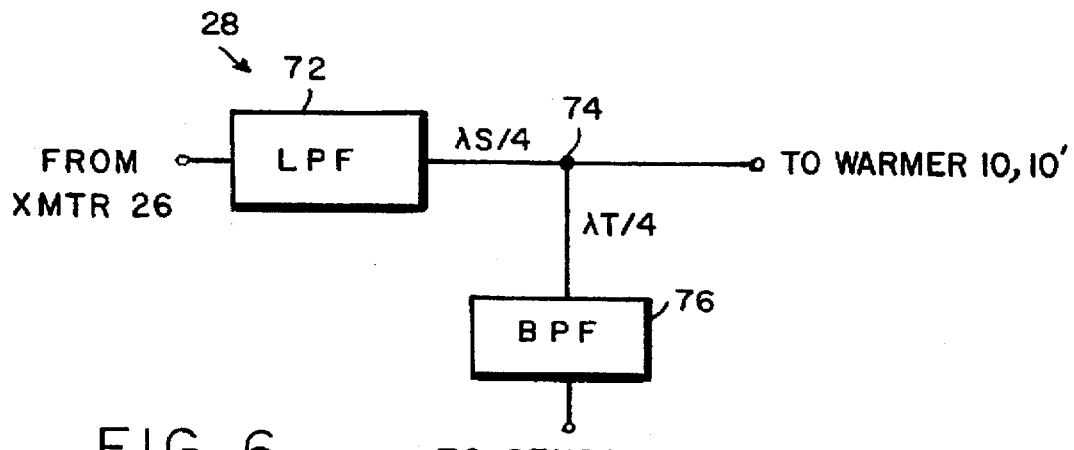
FIG. 6 is a diagrammatic view of the diplexer section of the FIG. 1 apparatus.

The diplexer 28 is depicted in FIG. 6. It separates the heating frequency (915 MHz) from the radiometer frequency (4.0 GHz) which allows the use of a common coaxial cable connection to the warmer 10, 10'. The diplexer includes a low pass filter 72 at the output port of the transmitter 26 which passes the 915 MHz signal while blocking the 4.0 GHz signal. Filter 72 is positioned a quarter wavelength from the junction 74 of the diplexer and provides, in essence, a quarter wavelength stub at 4.0 GHz. This creates a low loss, well matched stub at that frequency. The diplexer also includes a band pass filter 76 at the input port of sensor 32 located a quarter wavelength from junction 74. This filter allow low loss transmission over the band of the sensor 32, while blocking the 915 MHz transmitter signal from that sensitive radiometer.

In use, the warmer 10, 10' is connected in the line between the infusate source 16 and the patient 22, preferably as close to the patient as practicable. Unit 39 is then electrically connected to the warmer via connector 24.

When infusate flow commences, the warming apparatus may be actuated so that transmitter 26 delivers the microwave signal to the heating cavity 23 via diplexer 28. As noted previously, the conductor 64 in cavity 23 may be terminated by either an open circuit or a short circuit. In this way, the transmitter power not absorbed by the infusate I in cavity section 52 initially will be reflected back into that lossy liquid. The overall loss is enough to provide a proper impedance match to the transmitter 26.

As the infusate flowing through cavity section 52 absorbs energy, its temperature is elevated. That temperature is monitored on a non-invasive basis by the sensor 32 which, due to diplexer 28, detects only the energy associated with the temperature of the liquid being heated. The temperature indicating signal from sensor 32 may then be processed by processor 34 and used to control transmitter 26 to maintain the infusate temperature at a selected constant value, i.e., normal body temperature, despite variations in the fluid inlet temperature and flow rate and even at very low rates.

In certain applications where response time is not critical and/or where low cost is an important factor, the radiometer-type temperature sensor 32 may be replaced by one or more conventional thermistor or thermocouple sensors. Such a thermocouple sensor is shown in phantom at 80 in FIG. 2. The sensor 80 is mounted to the underside of circuit board 62 so that it is in contact with the infusate flowing through cavity section 52.

If a single sensor 80 is used, it is preferably located near the exit end of the warmer as shown so that the measured temperature is of the infusate leaving the warmer. The temperature measurement signal from a single thermocouple may be brought out of the warmer 10 on the center conductor 24b of connector 24. If more than one sensor 80 is present, e.g., one at each of the warmer inlet and outlet, the measured signals may be brought out of the warmer via a separate electrical connector mounted to or molded into housing 40 in the same manner as connector 24.

It will thus be seen that the objects set forth above, among those made apparent from the preceding description, are efficiently attained. Also, since certain changes may be made in the above construction without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention described herein.

What is claimed is:

1. Infusate warming apparatus comprising a housing defining an elongated microwave heating cavity having electrically conductive walls;

a printed circuit board separating said cavity lengthwise into first and second cavity sections, said printed circuit board including a fluid impervious, electrically insulating substrate and an elongated conductor run having opposite ends, said conductor run extending along said substrate and facing one of said cavity sections;

a fluid inlet into, and a fluid outlet from, said first cavity section so that infusate can flow through said first cavity section and connector means extending into said housing for coupling an external microwave signal of a selected frequency to, and a temperature sensing signal from, one end of said conductor run.

2. The apparatus defined in claim 1 wherein said conductor run follows a meandering path along the substrate.

3. The apparatus defined in claim 2 wherein said first cavity section has a footprint which is substantially the same as that of said conductor run.

4. The apparatus defined in claim 3 wherein the second cavity section is substantially a mirror image of the first cavity section.

5. The apparatus defined in claim 1 wherein said conductor run faces the second cavity section.

6. The apparatus defined in claim 1 wherein said connector means comprises a coaxial connector having outer and inner conductors, said outer conductor being connected electrically to said housing and said inner conductor being connected electrically to said one end of the conductor run.

7. Infusate warming apparatus comprising a housing defining an elongated microwave heating cavity having electrically conductive walls;

a printed circuit board separating said cavity lengthwise into first and second cavity sections, said printed circuit board including a fluid impervious, electrically insulating substrate and an elongated conductor run having opposite ends, said conductor run following a sinuous meandering path along the substrate and facing one of said cavity sections;

a fluid inlet into, and a fluid outlet from, said first cavity section so that infusate can flow through said first cavity section, and connector means extending into said housing for coupling an external microwave signal of a selected frequency to one end of said conductor run.

8. Infusate warming apparatus comprising a housing defining an elongated microwave heating cavity having electrically conductive walls;

a printed circuit board separating said cavity lengthwise into first and second cavity sections, said printed circuit board including a fluid impervious, electrically insulating substrate and an elongated conductor run having opposite ends, said conductor run extending along said substrate and facing one of said cavity sections;

a fluid inlet into and a fluid outlet from said first cavity section so that fluid can flow through said first cavity section, and conductor means extending into said housing for coupling an external microwave signal of a selected frequency to one end of said conductor run, the other end of said conductor run being connected electrically to said housing.

9. Infusate warming apparatus comprising an electrically conductive housing defining an elongated microwave heating cavity having opposite ends;

a printed circuit board separating said cavity lengthwise into first and second cavity sections, said printed circuit board including a fluid impervious, electrically insulating substrate and an elongated conductor run having opposite ends, said conductor run extending along said substrate and facing one of said cavity sections;

a fluid inlet into and a fluid outlet from said first cavity section so that infusate can flow through said first cavity section;

connector means extending into said housing for coupling an external microwave signal of a selected frequency to one end of said conductor run;

a microwave transmitter producing an output signal having a first frequency;

means for coupling the transmitter to said connector means so that the signal from the transmitter provides an energy field which heats the infusate flowing through said first cavity, and a sensor responsive to the temperature of the infusate flowing through said first cavity section and producing a temperature signal.

10. The apparatus defined in claim 9 wherein said sensor is a radiometric sensor responsive to a range of frequencies substantially higher than said first frequency, and said coupling means includes diplexer means connecting the transmitter and sensor to said connector means.

11. The apparatus defined in claim 9 and further including processing means responsive to said temperature signal for controlling said transmitter so as to maintain the infusate at a substantially constant outlet temperature despite variations in the infusate inlet temperature and flow rate.

12. The apparatus defined in claim 9 wherein said sensor comprises one or more thermocouples or thermistors exposed in said first cavity section.

13. Infusate warming apparatus comprising a housing defining an elongated microwave heating cavity having electrically conductive walls;

a printed circuit board separating said cavity lengthwise into first and second cavity sections, said printed circuit board including an electrically insulating substrate and a conductor run having opposite ends, said conductor run extending along the substrate and facing one of the cavity sections;

a fluid inlet into, and a fluid outlet from, said first cavity section, and connector means extending into said housing for coupling to said conductor run an external microwave signal of a selected frequency and from said conductor run a temperature-indicating signal having a different frequency from said selected frequency so that the conductor run and the fluid flowing through the second cavity section constitute a single transmission line.

14. The apparatus defined in claim 13 wherein the conductor run follows a meandering path along the substrate.

15. The apparatus defined in claim 14 wherein said first cavity section has a footprint which substantially matches that of the meandering conductor run.

16. The apparatus defined in claim 13 wherein said different frequency is substantially higher than said selected frequency.

17. The apparatus defined in claim 13 and further including a microwave transmitter producing an output signal having a first frequency;

means for coupling the transmitter to said connector means so that the signal from the transmitter provides an energy field which heats the infusate flowing through said first cavity, and a sensor connected to the connector means and responsive to the temperature of the infusate flowing through said first cavity section for producing a temperature signal.

* * * * *